United States Patent [19]

Addison

[11] Patent Number: 5,106,759
[45] Date of Patent: Apr. 21, 1992

[54] METHOD FOR COLLECTING RADON AND TESTING THEREFOR

[76] Inventor: Clark D. Addison, 113 Carter Lake Club, Carter Lake, Iowa 51510

[21] Appl. No.: 449,787

[22] Filed: Dec. 13, 1989

Related U.S. Application Data

[63] Continuation of Ser. No. 212,502, Jun. 28, 1988, abandoned.

[51] Int. Cl.⁵ .............................................. G01N 1/22
[52] U.S. Cl. ........................................ 436/178; 55/66; 55/75; 73/23.2; 73/31.02; 73/31.03; 422/88; 436/181; 436/182; 436/902
[58] Field of Search ............... 436/178, 182, 183, 902, 436/181; 422/88; 73/23, 863.21, 863.23, 23.2, 31.01, 31.02, 31.03; 55/66, 75; 250/255

[56] References Cited

U.S. PATENT DOCUMENTS

| | | | |
|---|---|---|---|
| 2,284,147 | 5/1942 | Herrick | 73/863.21 X |
| 4,327,575 | 5/1982 | Locker | 422/88 X |
| 4,406,823 | 9/1983 | Laurent et al. | 252/455 Z |
| 4,534,947 | 8/1985 | Vaughan | 423/329 |
| 4,717,560 | 1/1988 | Vaughan | 423/328 |
| 4,735,703 | 4/1988 | Sato et al. | 208/25 |
| 4,764,187 | 8/1988 | Abrams | 55/20 |
| 4,790,857 | 12/1988 | Miksch | 55/16 |
| 4,801,800 | 1/1989 | Scheible | 250/255 |
| 4,812,648 | 3/1989 | Perlman | 250/255 |
| 4,814,608 | 3/1989 | Dempsey et al. | 250/253 |

*Primary Examiner*—Robert J. Hill, Jr.

[57] ABSTRACT

A method for collecting radon in a confined area and testing therefor includes the initial step of providing a container with a molecular sieve material for attracting radon and placing the container in a confined area where radon is suspected to be present. The container has an open inlet end, into which radon will be attracted by the molecular sieve material in the container. The container is left in the confined area for a predetermined time, after which the container is removed so as to remove any radon present within the confined area and the molecular sieve is tested for radon.

1 Claim, 1 Drawing Sheet

U.S. Patent
Apr. 21, 1992
5,106,759
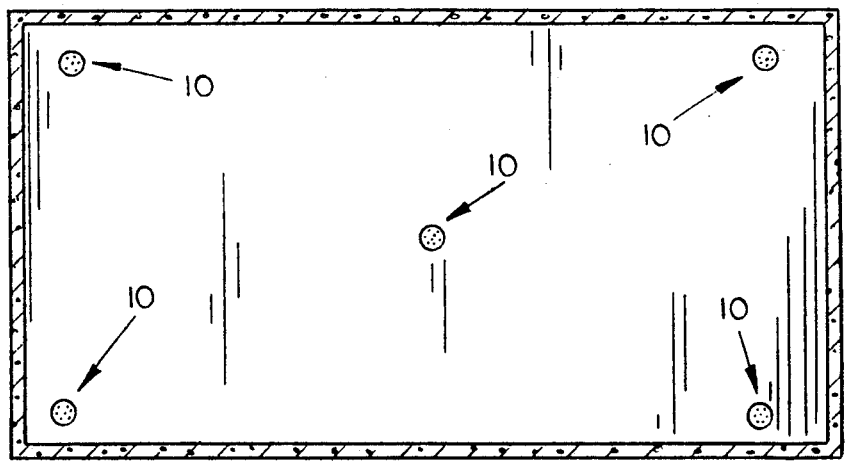
FIG. 1
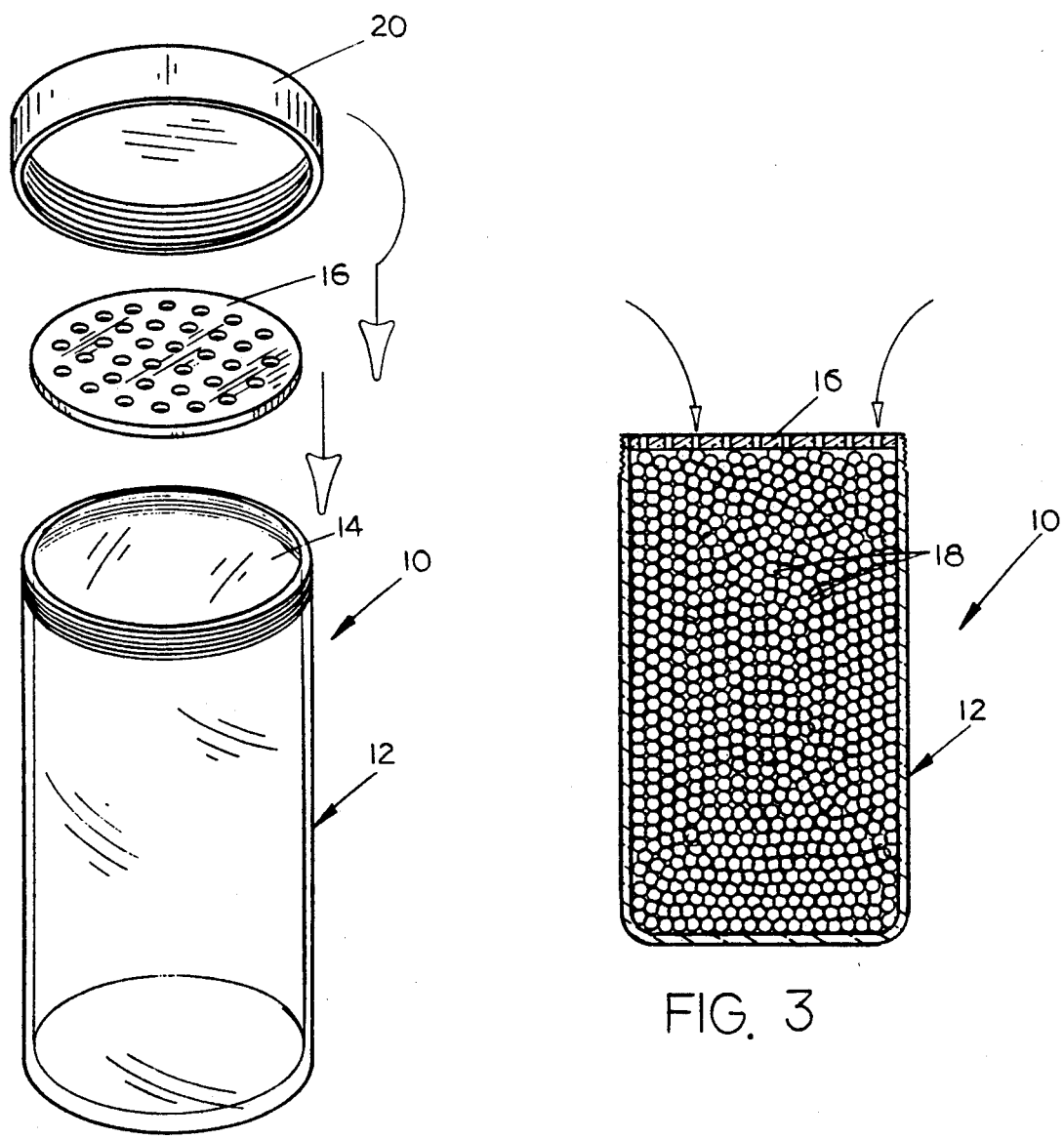
FIG. 2
FIG. 3

METHOD FOR COLLECTING RADON AND TESTING THEREFOR

CROSS-REFERENCE TO RELATED APPLICATION

This is a continuation application of Ser. No. 212,502, filed June 28, 1988, now abandoned.

BACKGROUND OF THE INVENTION

This invention relates to a method for collecting radon and testing therefor by providing a radon collection apparatus which may be used for removing radon from a confined area but which also may be used for the collection of radon within an area for subsequent testing.

Radon is a serious health threat to a large number of people. Recently, the United States Environmental Protection Agency (EPA) estimated that one out of every five homes in the United States had a radon level in excess of 4 Picocuries per liter—the level at which the EPA recommends corrective action be taken.

The only way to determine the radon level in a dwelling or the like is to test for it. Test kits are sold mainly through mail order by a large number of vendors, and the EPA has listed over 100 testing firms. Typically, the procedure is to place the detector in the area of the house, open the package's seal, and leave the device in place for the specified period of time. There are two types of radon detectors available: the so-called Alpha Track, or AT, and the Charcoal Cannister, or CC. ATs usually call for a one-to-three-month exposure period, which is helpful in averaging out short-term variations in radon concentration. CCs give a faster response, typically three days to one week.

There are drawbacks to both types of radon detectors. It is believed that the primary disadvantages to the AT type of detector is the length of time which is required to test the radon level in a particular area. A further disadvantage to an AT detector is that it is apparently sensitive to the movement of air and therefore would be affected by forced air heating and cooling systems within a dwelling.

The primary disadvantage with a CC type of detector is that it is very susceptible to humidity thereby requiring that the cannister be weighed before and after use and the difference in weight being utilized to calibrate the same. Further, it is believed that the CC detectors are susceptible to temperature changes. It is believed that when the CC type of detector is exposed to temperatures in excess of 100° F., the radon collected thereby is released into the atmosphere or into the area surrounding the detector.

It is therefore a principal object of the invention to provide an improved radon collection device.

A further object of the invention is to provide a radon collection apparatus which attracts and adsorbs radon in the vicinity of the apparatus so that the radon may be collected and removed from the area for disposal or testing.

A further object of the invention is to provide a radon collection device of the molecular sieve type.

A further object of the invention is to provide a radon collection apparatus which comprises a container filled with an alkali aluminosilicate of either the sodium form or calcium form of distal structure having an effective pore opening of from 3 angstroms to 13 angstroms.

Yet another object of the invention is to provide a radon collection apparatus which is economical of manufacture, easy to use and which may be repeatedly used after the collected radon has been purged therefrom.

These and other objects will be apparent to those skilled in the art.

DESCRIPTION OF THE DRAWINGS

FIG. 1 is a schematic view illustrating the manner in which the detectors of this invention are placed throughout the area which is being tested or the area from which the radon is being collected;

FIG. 2 is an exploded perspective view of the apparatus; and

FIG. 3 is a sectional view of the collection apparatus of this invention.

SUMMARY OF THE INVENTION

The method of this invention includes the steps of providing cylindrical container having an open upper end which is closed by a perforated plate to permit air to enter the same but which prevents the molecular sieve material in the container from passing therethrough. The molecular sieve material in the container may be comprised of an alkali aluminosilicate of either the calcium, potassium or sodium form such as a chemically inert aluminosilicate clay which is a montmorilonite clay which attracts and adsorbs the radon gas in the vicinity of the container. The container is placed in a confined area to collect the radon for subsequent disposal or to collect the radon in the area for testing the level of radon therein. The molecular sieve material is then subjected to high heat, whereby the radon gas may be purged therefrom so that the molecular sieve material is regenerated and may be reused.

DESCRIPTION OF THE PREFERRED APPARATUS AND METHOD

The collection apparatus of this invention is referred to generally by the reference numeral 10 and is comprised of a generally cylindrical container 12 having an open upper end 14. Upper end 14 is normally closed by some sort of a perforated plate 16 designed to permit air to pass therethrough while preventing the molecular sieve particles of the molecular sieve material 18 from passing therethrough. Prior to use, the plate 16 may be sealed by a suitable sealant or by the threaded cap 20.

It is recommended that the molecular sieve material have an effective pore opening of about 3 angstroms to 10 angstroms so that the molecular sieve material will adsorb molecules with a kinetic diameter of less than 10 angstroms and exclude those larger. The preferred pore opening is approximately 4–7 angstroms.

One manufacturer of the molecular sieve type of material just described is Zeochem, P.O. Box 35940, Louisville, Ky. 40232 and marketed under the trademark Zeochem ®.

The molecular sieve material 18 is preferably comprised of alkali aluminosilicate of either the potassium, sodium or calcium form such as manufactured and sold by Zeochem, P.O. Box 35940, Louisville, Ky. 40232, under the trademark Zeochem ®.

Four possible types of the molecular sieve material sold under the Zeochem ® trademark may be used, namely, Type 3A, Type 4A, Type 5A and Type 13X with Type 4A and Type 5A being the preferred material.

Zeochem ® molecular sieve Type 3A is an alkali alumionsilicate. It is the potassium form of the Type A crystal structure. Type 3A has an effective pore opening of about 3 angstroms. The chemical formula for Type 3A is $(K_2O \cdot Na_2O) \cdot Al_2O_3 \cdot 2SiO_2 \cdot XH_2O$.

Zeochem ® molecular sieve Type 4A is an alkali aluminosilicate. It is the sodium form of the Type A crystal structure. Type 4A has an effective pore opening of 4 angstroms. The chemical formula for Type 4A is $Na_2O \cdot Al_2O_3 \cdot 2SiO_2 \cdot XH_2O$.

Zeochem ® molecular sieve Type 5A is an alkali aluminosilicate. It is the calcium form of the Type A crystal structure. Type 5A has an effective pore opening of about 5 angstroms. The chemical formula for Type 5A is $4CaO \cdot Na_2O \cdot 5Al_2O_3 \cdot 10SiO_2 \cdot XH_2O$.

Zeochem ® molecular sieve Type 13X is also an aluminosilicate. It is the sodium for the Type X crystal structure. Type 13X has an effective pore opening of about 10 angstroms. The chemical formula for Type 13X is $5Na_2O \cdot 5Al_2O_3 \cdot 14SiO_2 \cdot XH_2O$.

Another form of the molecular sieve material which may be used is marketed under the trademark Desi Pak ® by United Desiccants of 6845 Westfield Avenue, Pennsauken, N.J. 08110-1572.

In use, the containers containing the molecular sieve material are placed throughout the area to be tested or in the area from which the radon is being collected as illustrated in FIG. 1. It is recommended and preferred that the containers not be adjacent hot or cold air registers or the like. When positioned, the seal covering the perforated plate 16 or the cap 20 is removed and the containers are allowed to remain in place for a predetermined length of time such as 24 or 48 hours. The molecular sieve material 18 attracts the air surrounding the container and causes the air to be drawn into the interior thereof where the radon is adsorbed by the particles of the molecular sieve material and trapped therein due to the pore size thereof. After the containers have been so positioned for the prescribed period of time, the containers are sealed and removed from the area for testing or for disposal. If the containers are being solely used for the collection of radon for disposal thereof, the containers would normally be allowed to remain in place for longer than the 24 to 48 hour period. After the containers have been tested, the material therein may be regenerated or purged by subjecting the containers to extremely high temperatures to purge the radon therefrom so that the containers may be subsequently reused.

Thus it can be seen that the invention accomplishes at least all of its stated objectives.

I claim:

1. A method of collecting radon in a confined area for the removal and testing thereof, comprising the steps of:

providing a container having an open inlet end closed by a removably sealable lid means, said container being filled with a molecular sieve material which has the inherent characteristics of attracting radon, said container having a perforated plate removably mounted in its upper end, the perforations being of a size smaller than said molecular sieve material to prevent removal of the material yet permit the flow of air therethrough, placing the container in the confined area, removing said sealable lid to reveal the open inlet end of said container, waiting a predetermined period of time with the container in the confined area, whereby at least a portion of any radon in said area will be attracted to the molecular sieve material in the container which will substantially remain therein, resealing said lid on said container, removing the container from the confined area so that the molecular sieve material may be tested for the presence of radon and so that any radon may be removed from said area, testing the molecular sieve material for radon, and subjecting the molecular sieve material to temperatures high enough to purge the material of radon.

* * * * *